United States Patent [19]

Jansen et al.

[11] Patent Number: 5,090,405

[45] Date of Patent: Feb. 25, 1992

[54] WATER-HARDENING POLYMER PREPARATIONS

[75] Inventors: Bernhard Jansen, Cologne; Hanns P. Müller, Bergisch-Gladbach; Roland Richter, Leverkusen; Wolfram Mayer, Odenthal-Glöbusch, all of Fed. Rep. of Germany

[73] Assignee: Bayer Aktiengesellschaft, Leverkusen, Fed. Rep. of Germany

[21] Appl. No.: 231,738

[22] Filed: Aug. 12, 1988

[30] Foreign Application Priority Data

Aug. 26, 1987 [DE] Fed. Rep. of Germany ....... 3728396
Apr. 15, 1988 [DE] Fed. Rep. of Germany ....... 3812481

[51] Int. Cl.$^5$ .................. A61L 15/07; A61F 5/04; A61F 13/04; B32B 27/40
[52] U.S. Cl. ..................... 602/8; 29/402.09; 138/141; 156/94; 156/185; 156/187; 156/189; 242/7.22; 427/407.3; 427/412; 427/412.1; 428/34.7; 428/36.1; 428/36.5; 428/230; 428/240; 428/242; 428/244; 428/253; 428/272; 428/273; 428/274; 428/283; 428/290; 428/306.6; 428/308.4; 428/913; 523/105; 524/188
[58] Field of Search ............... 428/423.1, 447, 260, 428/262, 500, 253, 272, 273, 274, 290, 306.6, 308.4, 913, 34.7, 36.1, 36.5; 524/188; 128/90; 523/105; 427/407.3, 412, 412.1

[56] References Cited

U.S. PATENT DOCUMENTS

| | | | |
|---|---|---|---|
| 4,096,162 | 6/1978 | Windemuth et al. | 260/448.2 |
| 4,667,661 | 2/1987 | Scholz et al. | 128/90 |
| 4,774,937 | 10/1988 | Scholz et al. | 428/23 |
| 4,856,502 | 8/1989 | Ersfeld | 428/253 |

*Primary Examiner*—James C. Cannon
*Attorney, Agent, or Firm*—Connolly & Hutz

[57] ABSTRACT

In a construction material comprising a flexible carrier substrate impregnated or coated with a water-hardening resin, the resin contains as an additive polyether polysiloxane polyurethanes of the formula

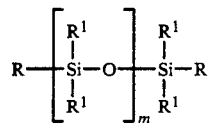

in which
$R^1$ is lower alkyl,
m is the average number of siloxane groups in the range from 5 to 25,
R is

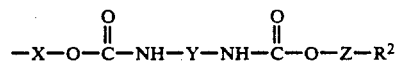

in which
X is lower alkylene,
Y is an aliphatic, cycloaliphatic, aromatic or araliphatic moiety, which is unsubstituted or substituted by further

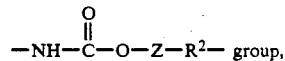

group, Z is a polyether moiety based on ethylene oxide units propylene oxide units, or both with the average number of ethylene oxide and propylene oxide units being in the range fro 10 to 100 and
$R^2$ is lower alkyl.

15 Claims, No Drawings

WATER-HARDENING POLYMER PREPARATIONS

The invention relates to water-hardening polymer preparations for construction materials, in particular for medical support dressings or industrial devices, which contain as additives polyether polysiloxane polyurethanes, a process for their preparation and their use.

The construction materials according to the invention generally consist of a carrier layer which is coated and/or impregnated with a water-hardening polymer preparation.

The construction materials according to the invention can in general be used for stiffening, shaping and sealing in the medical or industrial sector. In the medical sector they are preferably used as a gypsum substitute.

However, the construction materials according to the invention can also be used for the production of containers, filters, pipes, for joining construction elements, for manufacture of decorative or artistic articles, for stiffening purposes or as a filler or sealing material for joints and hollow spaces.

Construction materials which consist of a flexible carrier coated and/or impregnated with a water-hardening reactive resin are already known. An example which may be mentioned is DE-A-2,357,931, which describes construction materials of flexible carriers such as knitted fabrics, woven fabrics or non-wovens, which are coated or impregnated with water-hardening reactive resins, such as isocyanates or prepolymers modified by isocyanate groups.

The water-hardening polymer preparations which are known from DE-A-2,357,931 and the later subsequent developments have the disadvantage that they have poor modelling properties, in particular during the hardening phase since they then develop a high tackiness.

EP-A-0,221,669 attempts to solve this problem by adding lubricants. The sheet-like structures, for example orthopaedic bandages, described in EP-A-0,221,669 consist of a carrier coated with a water-hardening polymer preparation which is coated with a lubricant on most of its surface. The lubricants are compounds containing hydrophilic groups which are bonded covalently to the polymer, or they are additives which are incompatible with the polymer. The amount of lubricant chosen is such that a kinetic friction coefficient of the coated sheet-like structures of less than 1.2 is obtained. The sheet-like structures thus treated have a low tackiness. Among the incompatible, immiscible additives used are also polysiloxanes (page 8, line 28 to page 10, line 8).

To reduce the kinetic friction coefficient of the known materials significantly (for example to less than 1.2), it is necessary that a lubricant be present which has a hydrophilic groups which are bound to the polymer and/or contains an additive such as, for example, the polysiloxanes mentioned, which are immiscible with the polymer preparation, that is to say they must be applied separately.

Water-hardening polymer preparations for construction materials have been found which contain as additives polymer modifiers of the type of the polyether polysiloxane polyurethanes of the formula

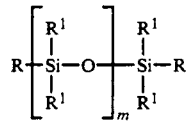 (I)

in which
R¹ stands for lower alkyl,
m stands for the average number of siloxane groups in the range from 5 to 25,
R stands for the radical

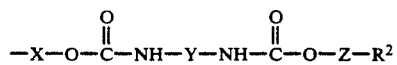

in which
X stands for a lower alkylene radical,
Y stands for an aliphatic, cycloaliphatic, aromatic or araliphatic radical,
Z stands for a polyether radical having ethylene oxide and/or propylene oxide groups, the average number of ethylene oxide and/or propylene oxide groups being in the range from 5 to 150 and
R² stands for lower alkyl,
it being possible for Y to be substituted by further

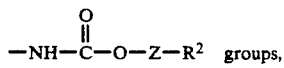 groups, in which
Z and R² have the abovementioned meaning.

The additives according to the invention are compatible with the polymer preparations and are completely miscible with them. They have a very high storage stability and do not separate into components even after storage for more than 12 months.

The advantage of the systems according to the invention is that they can be admixed as early as during the preparation of the reactive resins, which saves one processing step in comparison with known materials.

The preparations are easy to model during the hardening period, but they are not as slippery during the processing phase as the compounds of EP-A 221,669, where the lubricant is applied as a separate layer. The preparations according to the invention develop their good modelling properties only after they are wetted with water, which makes for convenient processing. The kinetic friction coefficient is then also less than 1.2, which demonstrates low tackiness.

In the context of the present invention the substituents of the polyether polysiloxane polyurethanes can in general have the following meaning:

In general, lower alkyl can denote a straight-chain or branched hydrocarbon radical having 1 to about 6 carbon atoms. Examples are methyl, ethyl, propyl, isopropyl, butyl, isobutyl, pentyl, isopentyl, hexyl and isohexyl. Preference is given to methyl and ethyl. Particular preference is given to methyl.

In general, lower alkylene can denote a divalent, straight-chain or branched hydrocarbon radical having 1 to about 6 carbon atoms. Examples are methylene, ethylene, propylene, isopropylene, butylene, isobutylene, pentylene, isopentylene, hexylene and isohexylene.

Preference is given to methylene, ethylene and propylene.

In general, an aliphatic radical can stand for a straight-chain or branched aliphatic hydrocarbon radical having 2 to 18, preferably 6 to 12, carbon atoms. Examples are the following radicals:

—(CH$_2$)$_6$—
—(CH$_2$)$_{12}$—

Preference is given to —(CH$_2$)$_6$—.

In general, a cycloaliphatic radical can be a cycloaliphatic hydrocarbon radical having 4 to 15, preferably 5 to 10, carbon atoms. Examples are the following cycloaliphatic hydrocarbon radicals:

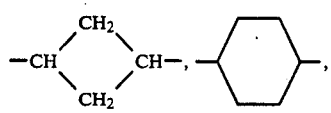

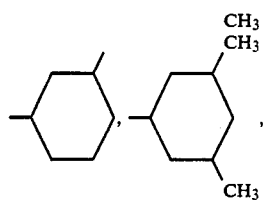

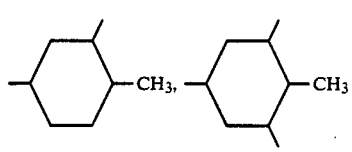

Preference is given to:

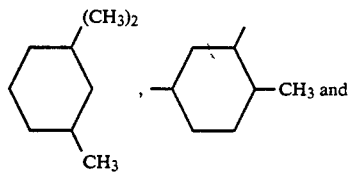

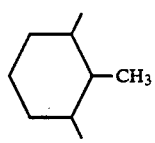

In general, an aromatic radical can be an aromatic hydrocarbon radical having 6 to 15, preferably 6 to 13, carbon atoms. Examples of aromatic radicals are: phenyl, naphthyl and biphenyl. Phenyl is preferred.

In general, an araliphatic radical can be an araliphatic hydrocarbon radical having 8 to 15, preferably 8 to 13, carbon atoms. Examples of araliphatic radicals are: benzyl,

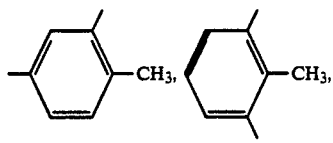

-continued

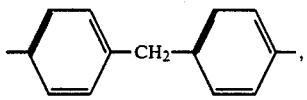

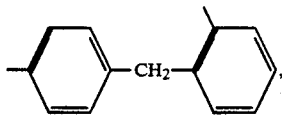

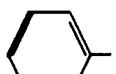

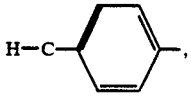

Preference is given to:

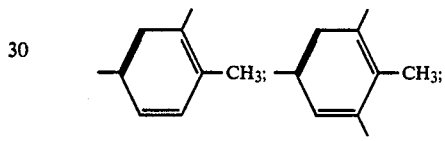

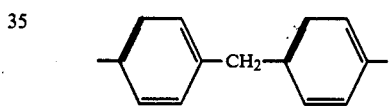

The aliphatic, cycloaliphatic, aromatic and araliphatic radicals (Y) mentioned can, if desired, be substituted by further, preferably by two, particularly preferably by one, further substituents of the formula

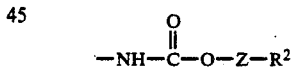

Specifically, examples of radicals for Y are those which are derived from the following low-molecular-weight polyisocyanates:

Suitable low-molecular-weight polyisocyanates of this type are, for example, hexamethylene diisocyanate, 1,12-dodecane diisocyanate, cyclobutane 1,3-diisocyanate, cyclohexane 1,3- and 1,4-diisocyanate and also any desired mixtures of these isomers, 1-isocyanato-3,3,5-trimethyl-5-isocyanatomethylcyclohexane, 2,4- and 2,6-hexahydrotoluylene diisocyanate and also any desired mixtures of these isomers, hexahydro-1,3- and/or -1,4-phenylene diisocyanate, perhydro-2,4'- and/or -4,4'-diphenylmethane diisocyanate, 1,3- and 1,4-phenylene diisocyanate, 2,4- and 2,6-toluylene diisocyanate and also any desired mixtures of these isomers, diphenyl methane 2,4'- and/or 4,4'-diisocyanate, naphthylene 1,5-diisocyanate, triphenylmethane 4,4',4''-triisocyanate or polyphenylpolymethylene polyisocyanates, such as are obtained by aniline-formaldehyde condensation followed by phosgenation.

Suitable higher-molecular-weight polyisocyanates are modification products of such simple polyisocyanates, that is polyisocyanates having, for example, isocyanurate, carbodiimide, allophanate, biuret or uretdione structural units, such as can be prepared by processes of the prior art which are known per se from the simple polyisocyanates of the above mentioned general formula which have been mentioned as examples.

Particularly preferred polyisocyanate components according to the invention are the industrial polyisocyanates which are customary in polyurethane chemistry, that is hexamethylene diisocyanate, 2,4- and 2,6-toluylene diisocyanate, 1-isocyanato-3,3,5-trimethyl-5-isocyanatomethyl cyclohexane (isophorone diisocyanate, abbreviated: IPDI), 4,4'-diisocyanatodicyclohexylmethane, 4,4'-diisocyanatodiphenylmethane, mixtures thereof with the corresponding 2,4' and 2,2' isomers, polyisocyanate mixtures of the diphenylmethane series such as can be obtained by phosgenation of aniline/formaldehyde condensates in a manner known per se, the modification products of these industrial polyisocyanates which have biuret or isocyanurate groups and also any desired mixtures of such polyisocyanates. Isocyanates having aromatically bound NCO groups are preferred according to the invention. A polyisocyanate component particularly preferred according to the invention is 2,4- and 2,6-toluylene diisocyanate and/or mixtures of both isomers.

In general, the polyether radical (Z) consists of ethylene oxide groups and/or propylene oxide groups. Preferably, it consists of ethylene oxide groups and propylene oxide groups. The average total number of ethylene oxide groups and propylene groups is usually in the range from about 5 to about 150, preferably from 10 to 100. In the preferred case where the polyether radical consists of ethylene oxide groups and propylene oxide groups, the weight ratio of ethylene oxide to propylene oxide is in general 10:90% to 80:20%, preferably 20:80% to 75:25%.

The ethylene oxide groups and propylene oxide groups can be arranged randomly, alternately or in blocks. Preference is given to a random distribution.

Preferably, the water-hardening polymer preparations according to the invention can contain as additives polyether polysiloxane polyurethanes of the formula (I) in which R$^1$ stands for methyl or ethyl,
m stands for the average number of siloxane groups in the range from 5 to 25,
R stands for the radical

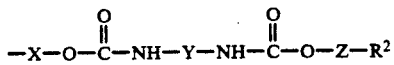

in which
X stands for alkylene (C$_1$ to C$_4$),
Y stands for an aliphatic hydrocarbon radical having 2 to 18 carbon atoms, a cycloaliphatic hydrocarbon radical having 4 to 15 carbon atoms, an aromatic hydrocarbon radical having 6 to 15 carbon atoms or an araliphatic hydrocarbon radical having 8 to 15 carbon atoms,
Z stands for a polyether radical having ethylene oxide groups and propylene oxide groups, the average number of ethylene oxide groups and propylene oxide groups being in the range from 10 to 100, and R$^2$ stands for alkyl (C$_1$ to C$_4$),
the weight ratio of ethylene oxide groups to propylene oxide groups being 10:90% to 80:20%, and it being possible for
Y to be substituted by 1 or 2 further

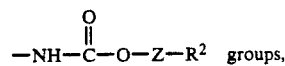

in which
Z and R$^2$ have the abovementioned meaning.

Particularly preferably, the water-hardening polymer preparations according to the invention can contain as additives polyether polysiloxane polyurethanes of the formula (I) in which
R$^1$ stands for methyl or ethyl,
m stands for the average number of siloxane groups in the range from 5 to 25,
R stands for the radical

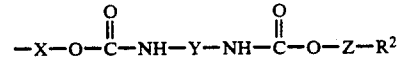

in which
X stands for alkylene (C$_1$ to C$_4$)
Y stands for an aliphatic hydrocarbon radical having 6 to 10 carbon atoms, a cycloaliphatic hydrocarbon radical having 5 to 10 carbon atoms, an aromatic hydrocarbon radical having 6 to 13 carbon atoms or an araliphatic hydrocarbon radical having 8 to 13 carbon atoms,
Z stands for a polyether radical having ethylene oxide groups and propylene oxide groups, the average number of ethylene oxide groups and propylene oxide groups being in the range from 10 to 100
R$^2$ stands for the alkyl (C$_1$ to C$_4$),
the weight ratio of ethylene oxide groups to propylene oxide groups being 10:90% to 80:20%, and it being possible for
Y to be substituted by a further

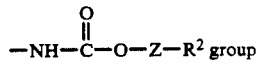

in which
Z and R$^2$ have the abovementioned meaning.

The group of polyether polysiloxane polyurethane used as additives is known per se (DE-A 2,558,523, U.S. Pat. No. 4,096,162); they are used as stabilizers for polyurethane foams.

The polyether polysiloxane polyurethanes can be prepared by reacting in the isocyanate OCN-Y-NCO with a monohydroxy functional polyether HO-Z-R$^2$ and then reacting the reaction product OCN—Y—NH—CO—O—Z—R$^2$ with a bishydroxy-alkyldialkylpolysiloxane

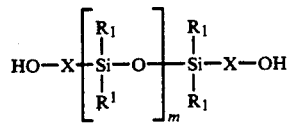

in which
X, Y, Z, R¹, R² and m have the abovementioned meaning.

The water-hardening polymer preparations according to the invention in general contain 0.1 to 10% by weight, preferably 0.5 to 8% by weight, of polyether polysiloxane polyurethanes, based on the polymer resin, the intention being that the kinetic friction coefficient is smaller by 0.5 or more, than that without the presence of the appropriate additives.

It is, of course, possible for the water-hardening polymer preparations according to the invention to contain as additives more than one of the said polyether polysiloxane polyurethanes according to the invention.

Preferably, the water-hardening polymer preparations are resins based on polyurethane or polyvinyl resin. Polyisocyanates or prepolymers having tree isocyanate groups (polyurethanes) are particularly preferred.

According to the invention, suitable water-hardening polyisocyanates and polyurethanes are all organic polyisocyanates known per se, that is any desired compounds or mixtures of compounds which contain at least two organically bound isocyanate groups per molecule. These include not only low-molecular-weight polyisocyanates having a molecular weight under 400 but also modification products of such low-molecular-weight polyisocyanates having a molecular weight which can be calculated from the functionality and the proportion of functional groups, for example of 400 to 10,000, preferably 600 to 8,000, and in particular 800 to 5,000. Suitable examples of low-molecular-weight polyisocyanates are those of the formula

Q(NCO)$_n$, in which
n is 2 to 4, preferably 2 to 3, and
Q denotes an aliphatic hydrocarbon radical having 2 to 18, preferably 6 to 10 C atoms, a cycloaliphatic hydrocarbon radical having 4 to 15, preferably 5 to 10 C atoms, an aromatic hydrocarbon radical having 6 to 15, preferably 6 to 13, C atoms, or an araliphatic hydrocarbon radical having 8 to 15, preferably 8 to 13, C atoms.

Suitable low-molecular-weight polyisocyanates of this type are, for example, hexamethylene diisocyanate, 1,12-dodecane diisocyanate, cyclobutane 1,3-diisocyanate, cyclohexane 1,3- and 1,4-diisocyanate and also any desired mixtures of these isomers, 1-isocyanato-3,3,5-trimethyl-5-isocyanatomethylcyclohexane, 2,4- and 2,6-hexahydrotoluylene diisocyanate and also any desired mixtures of these isomers, hexahydro-1,3- and/or -1,4-phenylene diisocyanate, perhydro-2,4'- and/or -4,4'-diphenylmethane diisocyanate, 1,3- and 1,4-phenylene diisocyanate, 2,4- and 2,6-toluylene diisocyanate and also any desired mixtures of these isomers, diphenyl methane 2,4'- and/or -4,4'-diisocyanate, naphthylene 1,5-diisocyanate, triphenylmethane 4,4',4''-triisocyanate or polyphenyl-polymethylene polyisocyanates, such as are obtained by aniline/formaldehyde condensation followed by phosgenation.

Suitable higher-molecular-weight polyisocyanates are modification products of such simple polyisocyanates, that is polyisocyanates having, for example, isocyanurate, carbodiimide, allophanate, biuret or uretdione structural units, such as can be prepared by processes of the prior art which are known per se from the simple polyisocyanates of the abovementioned general formula which have been mentioned as examples. Among the higher-molecular-weight, modified polyisocyanates, in particular the prepolymers, known from polyurethane chemistry and having terminal isocyanate groups of the molecular weight range of 400 to 10,000, preferably 600 to 8,000, and in particular 800 to 5,000 are of interest. These compounds are prepared in a manner known per se by reaction of excess amounts of simple polyisocyanates of the type mentioned as examples with organic compounds having at least two groups which are reactive towards isocyanate groups, in particular organic polyhydroxyl compounds. Suitable polyhydroxyl compounds of this type are not only simple polyhydric alcohols such as, for example, ethylene glycol, trimethylolpropane, propanediol-1,2 or butanediol-1,2, but in particular higher-molecular-weight polyether polyols and/or polyester polyols of the type known per se from polyurethane chemistry and having molecular weights of 600 to 8,000, preferably 800 to 4,000, and which have at least two, as a rule 2 to 8, but preferably 2 to 4 primary and/or secondary hydroxyl groups. It is, of course, also possible to use those NCO prepolymers which have been obtained, for example, from low-molecular-weight polyisocyanates of the type mentioned as examples and less preferred compounds having groups which are reactive towards isocyanate groups such as, for example, polythioether polyols, polyacetals having hydroxyl groups, polyhydroxy polycarbonates, polyesteramides having hydroxyl groups or copolymers of olefinically unsaturated compounds having hydroxyl groups. Compounds having groups which are reactive towards isocyanate groups, in particular hydroxyl groups, and which are suitable for preparing the NCO prepolymers are, for example, those compounds which have been disclosed as examples in U.S. Pat. No. 4,218,543, column 7, line 29 to column 9, line 25. To prepare the NCO prepolymers, these compounds having groups which are reactive towards isocyanate groups are reacted with simple polyisocyanates of the type mentioned above as examples while maintaining an NCO/OH equivalent ratio of >1. In general, the NCO prepolymers have an NCO content of 2.5 to 30, preferably 6 to 25% by weight. From this it immediately follows that in the context of the present invention "NCO prepolymers" or "prepolymers having terminal isocyanate groups" are to be understood as meaning not only the reaction products as such but also their mixtures with excess amounts of unconverted starting polyisocyanates, which are often also called "semiprepolymers".

Particularly preferred polyisocyanate components according to the invention are the industrial polyisocyanates which are customary in polyurethane chemistry, that is hexamethylene diisocyanate, 1-isocyanato-3,3,5-trimethyl-5-isocyanatomethylcyclohexane (isophorone diisocyanate, abbreviated: IPDI), 4,4'-diisocyanatodicyclohexylmethane, 4,4'-diisocyanatodiphenylmethane, mixtures thereof with the corresponding 2,4' and 2,2' isomers, polyisocyanate mixtures of the diphenylmethane series such as can be obtained by phosgenation of aniline/formaldehyde condensates in a manner known per se, the modification products of these industrial polyisocyanates which have biuret or isocyanurate groups and, in particular, NCO prepolymers of the type mentioned which, on the one hand, are based on these industrial polyisocyanates and, on the other hand, the simple polyols mentioned as examples and/or polyether polyols and/or polyester polyols, and also any desired mixtures of such polyisocyanates. Isocyanates having aromatically bound NCO groups are preferred according to the invention. A polyisocyanate component particularly preferred according to the invention is partially carbodiimidized diisocyanatodiphenylmethane which, as a result of the addition of monomeric diisocyanate to the carbodiimide structure, also has uretonimine groups.

The water-hardening polyurethanes can contain catalysts which are known per se. These catalysts can be, in particular, tert. amines which catalyze the isocyanate-/water reaction and not a self-reaction (trimerization, allophanatization) (DE-A 2,357,931). Examples which may be mentioned are polyethers containing tert. amines (DE-A 2,651,089), low-molecular-weight tert. amines such as

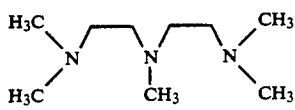

or dimorpholine diethyl ether or bis-(2,6-dimethylmorpholino)diethyl ether (WO 86/01397). The proportion of catalyst, based on tert. nitrogen, is in general 0.05 to 0.5% by weight, based on the polymer resin.

Water-hardening polyvinyl resins can be, for example, vinyl compounds which consist of a hydrophilic prepolymer having more than one polymerizable vinyl group in which a solid, insoluble vinyl redox catalyst is incorporated, one component of which is surrounded by a water-soluble or water-permeable sheath. Such a redox catalyst is, for example, sodium bisulphite/copper(II) sulphate, in which, for example, copper sulphate is encapsulated by poly-2-hydroxyethyl methylacrylate.

Polyvinyl resins are described, for example, in EP-A-0,136,021.

The water-hardening polymer preparations can contain additives known per se such as, for example, flow-control agents, thixotropic agents, antifoams and other known lubricants.

Furthermore, the synthetic resins can be coloured or, if desired, contain UV stabilizers.

Examples of additives which may be mentioned are: polydimethylsiloxanes, calcium silicates of the aerosil type, polywaxes (polyethylene glycols), UV stabilizers of the ionol type (DE-A 2,921,163), coloured pigments such as soot, iron oxides, titanium dioxide or phthalocyanines.

The additives which are, in particular, suitable for polyurethane prepolymers are described in Kunststoff Handbuch (Handbook of Plastics), volume 7, Polyurethanes, pages 100 to 109 (1983). They are generally added in an amount of 0.5 to 5% (based on the resin).

Carrier materials can be solid or porous films or else foams made of natural or synthetic materials (for example polyurethane), primarily air-permeable, flexible sheet-like structures based on textiles, preferably having a basis weight of 20 to 1,000 g/m², in particular of 30 to 500 g/m². Examples of sheet-like structures are:

Carrier material
1. Textile woven fabrics and knitted fabrics having a basis weight of 20 to 400 g/m², preferably 40 to 250 g/m², 25 to 100 courses per 10 cm, preferably 30 to 75 courses per 10 cm and 30 to 90 wales per 10 cm, preferably 40 to 80 wales per 10 cm. The textile woven fabric or knitted fabric can be made of any desired natural or synthetic yarns. Preferably, yarns are used which consist of cotton, polyester, polyacrylate, polyamide or elastane fibres or of mixtures of the abovementioned. Particular preference is given to textile carriers made of the abovementioned yarns which have an elongation in the longitudinal direction of 10 to 100% and/or in the transverse direction of 20 to 300%.

2. Glass fibre woven fabrics or knitted fabrics having a basis weight of 60 to 500 g/m², preferably 100 to 400 g/m², made of glass fibre yarns having an E modulus of 7,000 to 9,000 (daN/mm²), and a number of threads of 3 to 10, preferably 5 to 7 in the longitudinal direction and a number of threads of 3 to 10, preferably 4 to 6, in the transverse direction per centimetre of glass fibre woven fabric and which have a longitudinal elasticity of 10 to 30% by virtue of a particular type of heat treatment are preferred. The knitted fabrics can be both sized and unsized.

3. Non-bonded or bonded or needled fibre webs based on inorganic and, preferably, organic fibres having a basis weight of 30 to 400 g/m², preferably 50 to 200 g/m².

For the production of construction materials according to the invention in the form of shells or splints, fibre webs having basis weights up to 1,000 g/m² are also possible. Carrier materials which are suitable according to the invention are, for example, also described in U.S. Pat. No. 4,134,397, U.S. Pat. No. 3,686,725, U.S. Pat. No. 3,882,857, DE-A-3,211,634 and EP-A-61,642.

In the construction materials according to the invention, the carrier material is coated and/or impregnated with an amount of 25 to 80% by weight, preferably of 30 to 75% by weight, of water-hardening polymer preparation, based on the entire material.

A process for the preparation of water-hardening polymer preparations for construction materials has also been found, characterized in that a water-hardening reactive resin is mixed with a polyether polysiloxane polyurethane additive of the formula

in which
R¹ stands for lower alkyl
m stands for the average number of siloxane groups in the range from 5 to 25,
R stands for the radical

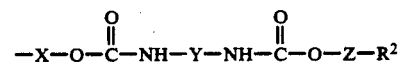

in which
X stands for a lower alkylene radical,
Y stands for an aliphatic, cycloaliphatic, aromatic or araliphatic radical,
Z stands for a polyether radical having ethylene oxide and/or propylene oxide groups, the average number of ethylene oxide and/or propylene oxide groups being in the range from 5 to 150 and R² stands for lower alkyl, it being possible for Y to be substituted by further

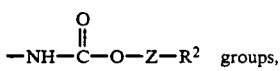 groups, in which

Z and R² have the abovementioned meaning, catalysts and further auxiliaries and additives are added and the mixture is then distributed homogeneously over the surface of the carrier material.

The process according to the invention is carried out in the absence of moisture. Preferably, it is carried out at a relative humidity of <2% (at 21° C.), particularly preferably at <1% (at 21° C.).

For the coating or impregnation, the polymer preparation can be dissolved in an inert solvent which is again evaporated after the coating process.

Inert solvents can be for example chlorinated hydrocarbons such as methylene chloride, trichloroethane or chloroform, ketones such as acetone and methyl ethyl ketone, esters such as ethyl acetate and butyl acetate, aromatics such as toluene, xylene or appropriate derivatized types having no hydrogen activatable with a Zerewitinoff reagent.

The construction materials according to the invention can be prepared, for example, as follows:

In general, the carrier material is run over a roll and impregnated with the polymer preparation in the absence or presence of a solvent. Immediately after the coating or impregnating step, the material is wound up in the desired length (as a rule, 2 to 11 m) on suitable centres and sealed in an air- and water-tight film (for example made of plastic aluminium laminate) or in other completely tight containers, such as are described in DE-A-2,357,931, DE-A-2,651,089 and DE-A-3,033,569.

Immediately before use, the material is removed from the package and wrapped around the relevant object or applied in some other way.

For hardening, the preparations according to the invention are brought into contact with water, or, if desired, merely with air moisture.

As a rule, the hardening process is short (about 3 to 15 minutes). During this time, the preparations according to the invention have surprisingly good modelling properties. They hardly show any tackiness and their kinetic friction coefficient is in general less than 1.0.

The polymer modifications according to the invention, which significantly facilitate the processing of the coated carrier material, do not affect the range of properties of the hardened construction materials with respect to hardness, elongation at break and interlayer cohesion.

EXAMPLE 1

Preparation of the Reactive Resin Additive According to the Invention

An apparatus consisting of a three-neck flask equipped with stirrer, dropping funnel and reflux condenser in 250 ml of absolute methylene chloride is charged initially with 94.2 g of toluylene 2,4-and 2,6-diisocyanate mixture in an isomer ratio of 80:20

1200 g of a monofunctional polyether, initiated with n-butanol and having a mixed block consisting of 15% of propylene oxide and 65% of ethylene oxide and a terminal block consisting of 20% of ethylene oxide (average molecular weight: 2440 g/mol), are slowly added dropwise to the initial charge which is kept under reflux. After the addition is completed, heating under reflux is continued for half an hour.

153 g of a polydimethylsiloxane having a bishydroxymethyl function and an average molecular weight of 566 g/mol are then added, and the reaction mixture is heated under reflux for another 2 hours. The entire reaction mixture is worked up by removing the solvent in a rotary evaporator and can now be used as an additive.

EXAMPLE 2

Preparation of a Water-Hardening Reactive Resin According to the Invention (Using the Additive According to the Invention)

A 10-l sulphonation vessel equipped with a stainless-steel horseshoe stirrer is charged with 6.48 kg of isocyanate (bis-(4-isocyanatophenyl)methane, which contains carbodiimidized portions [NCO content=29%]). 7.8 g of a polydimethyl siloxane having $\eta$=30,000 mPas and 4.9 g of benzoyl chloride and then 1.932 kg of a polyether prepared by propoxylation of propylene glycol (OH number=112 mg of KOH/g), 1.29 kg of a polyether prepared by propylation of propylene glycol (OH number=250 mg of KOH/g) and 190 g of dimorpholinodiethyl ether are then added. After 30 minutes, the reaction temperature reaches 45° C., after 1 hour a maximum temperature of 56° C. is reached and the isocyanate content is 14.2%. 500 g of the additive described in Example 1, are then added to the reaction mixture and the mixture is stirred until it is homogeneous. The final isocyanate content is 13.2% and the viscosity is 19,950 mPa.s.

EXAMPLE 3

Preparation of a Water-Hardening Reactive Resin (Comparative Example Without Additive)

An apparatus analogous to Example 2 is charged with 6.48 kg of isocyanate (bis(4-isocyanatophenyl) urethane, which contains carbodiimidized portions [NCO content=29%]). 7.8 g of a polydimethyl siloxane having $\eta_{25}$=30,000 mPa.s. and 4.9 g of benzoyl chloride and of propylene glycol (OH number=112 mg of KOH/g), 1.29 kg of a polyether prepared by propoxylation of glycerol/OH number=250 mg of KOH/g) and 190 g of dimorpholinodiethyl ether are then added. After 30 minutes, the reaction temperature reaches 42° C., after 1 hour the maximum temperature of 48° C. is reached and the isocyanate content is 13.6%. The viscosity is 17,800 mPa.s.

EXAMPLE 4

Preparation of a Water-Hardening Reactive Resin According to the Invention (Using the Additive According to the Invention)

A 10-l sulphonation vessel equipped with a stainless-steel horseshoe stirrer is charged with 6.5 kg of isocyanate (bis-(4-isocyanatophenyl) methane, which contains carbodiimidized portions (NCO content 29%) and the mixture is initially heated to about 50° C. 150 g of a UV stabilizer (a cyanoalkylindole derivative) are added and the mixture is stirred until the entire solid is dissolved. After cooling to room temperature, 3.5 kg of propoxylated triethanolamine (OH number=150 mg of KOH/g) are added over a period of 10 minutes. After a brief increase in temperature to 55° C. after 55 minutes, the temperature drops again and the isocyanate content reaches 13.4% after 2 hours. After 534.2 g of the additive described in Example 1 have been added the reaction mixture is stirred until it is homogeneous, and its viscosity is 19,056 mPa.s (25° C.).

EXAMPLE 5

Preparation of a Water-Hardening Reactive Resin (Comparative Example Without Additive)

A 10 l sulphonation vessel with stainless-steel horseshoe stirrer is charged with 6.5 kg of isocyanate (bis-(4-isocyanatophenyl) methane, which contains carbodiimidized portions [NCO content=29%]), and the mixture is initially heated to about 50° C. 150 g of a UV stabilizer (a cyanoalkylindole derivative) are added and the mixture is stirred until the entire solid is dissolved. After cooling to room temperature, 3.5 kg of propoxylated triethanolamine (OH number=150 mg of KOH/g) are added over a period of 10 minutes. After a brief increase in temperature to 55° C. after 55 minutes, the temperature drops again and the isocyanate content reaches 13.4% after 2 hours. The isocyanate content of the finished prepolymer is 12.7%, and the viscosity is 14,640 mPa.s (25° C.).

EXAMPLE 6

Preparation of Test Dressings Using the Reactive Resins of Examples 2-5

6a) A glass fibre mixture (width 10.0 cm, basis weight about 290 g/m²), which has an elongation in the longitudinal direction of about 65% (a detailed description of this knitted fabric can be found in U.S. Pat. No. 4,609,578), is coated with 80% by weight (based on the knitted fabric) of the resin from Example 2. The coating is carried out in an atmosphere whose relative humidity is characterized by a water dew point of less than −20° C. The resin is homogeneously applied to the knitted fabric using a suitable roll impregnation apparatus. A suitable apparatus is described in detail in U.S. Pat. No. 4,427,002. After coating, 3.66 m of this band are wound on a plastic centre, 1 cm in diameter, and sealed in a water vapour-impermeable film.

6b) Analogously to Example (6a), the glass fibre knitted fabric is coated with 80% by weight (based on the knitted fabric) of the resin from Example 3 and packed.

6c) Analogously to Example (6a), the glass fibre knitted fabric is coated with 70% by weight (based on the knitted fabric) of the resin from Example 4 and packed.

6d) Analogously to Example (6a), the glass fibre knitted fabric is coated with 70% by weight (based on the knitted fabric) of the resin with Example 5 and packed.

6e) Analogously to Example (6a), a polyester knitted fabric (width 10.0 cm, basis weight 118 g/m²), which has an elongation of about 55% in the longitudinal direction and an elongation of about 90% in the transverse direction and has a textured polyester polyfilament yarn (167 dtex, f 30×1) in the wale and a high-tenacity polyester polyfilament yarn (550 dtex, f 96, standard shrinkage) in the course, is coated with 150% by weight (based on the knitted fabric) of the resin from Example 2 and packed.

6f) Analogously to Example (6a), the polyester knitted fabric described in Example (6e) is coated with 150% by weight (based on the knitted fabric) of the resin from Example 2 and packed.

EXAMPLE 7

Determination of the Kinetic Friction Coefficient of the Coated Carrier Materials 6a to 6f In complete analogy to EP 221,669, the kinetic friction coefficient was determined in accordance with the ASTm D-1894 test using an apparatus from Instron Corp. (Instron Coefficient of Friction Fixture; Catalogue No. 2810-005) and the stainless-steel carriage described in EP-A 221,669, page 13.

The test dressings were removed from the package after 1 month and readied and measured as described in EP-A 221,669, page 14, 15. The force measurement was carried out using a ZWICK Universal Testing Machine, type 1484.

|  | Kinetic friction coefficient |
|---|---|
| Comparative samples: | |
| Scotchcast ® | 2.0 |
| (without lubricant, see | |
| EP 221,669, page 17) | |
| Scotchcast ® Plus | 0.3 |
| (with lubricant, ethylene | |
| oxide in reactive resin, | |
| 4.7% of polydimethylsiloxane | |
| addition) | |
| Examples (according to | |
| the invention) | |
| 6a | 0.8 |
| 6b | 1.5 |
| 6c | 0.7 |
| 6d | 1.6 |
| 6e | 0.3 |
| 6f | 0.8 |

What is claimed is:

1. In an improved construction material comprising a flexible carrier substrate impregnated or coated with a water-hardening polyisocyanate, polyurethane or polyvinyl polymer preparation, the improvement comprises said preparation containing as an additive 0.1 to 10% by weight polyether polysiloxane polyurethanes of the formula

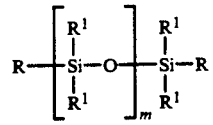

in which
R¹ is lower alkyl,
m is the average number of siloxane groups in the range from 5 to 25,
R is

in which
X is lower alkylene,
Y is an aliphatic, cycloaliphatic, aromatic or araliphatic moiety, which is unsubstituted or substituted by further

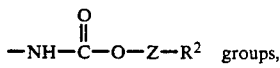 groups,

Z is a polyether moiety based on ethylene oxide, units propylene oxide units, or both with the average number of ethylene oxide and propylene oxide units being in the range from 10 to 100 and $R^2$ is lower alkyl.

2. Construction material according to claim 1 wherein the preparation contains polyether polysiloxane polyurethanes, in which
$R^1$ is methyl or ethyl,
m is the average number of siloxane groups in the range from 5 to 25,
R is

in which
X is alkylene having 1 to 4 carbon atoms,
Y is an aliphatic hydrocarbon moiety having 2 to 18 carbon atoms, a cycloaliphatic hydrocarbon moiety having 4 to 15 carbon atoms, and wherein Y is unsubstituted by further

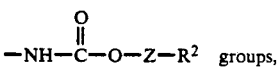 groups,

Z is a polyether moiety based on ethylene oxide units and propylene oxide units with the average number of ethylene oxide units and propylene oxide units being in the range from 5 to 150 and with the weight ratio of ethylene oxide units to propylene oxide units being 10:90 to 80:20, and $R^2$ is alkyl having 1 to 4 carbon atoms.

3. Construction material according to claim 2 wherein Y is an aliphatic hydrocarbon moiety having 6 to 10 carbon atoms, a cycloaliphatic hydrocarbon moiety having 5 to 10 carbon atoms, an aromatic hydrocarbon moiety having 6 to 13 carbon atoms, and wherein Y is unsubstituted or substituted by further

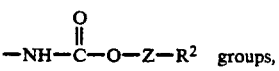 groups, and wherein Z is a polyether moiety based on ethylene oxide units and propylene oxide units with the average number of ethylene oxide units and propylene oxide units being in the range from 10 to 100 and the weight ratio of ethylene oxide units to propylene oxide units being 10:90 to 80:20.

4. Construction material according to claim 1 wherein the preparation contains 0.5 to 8% by weight of polysiloxane.

5. Construction material according to claim 1 wherein the preparation contains polyisocyanates or prepolymers thereof having more than two isocyanate groups.

6. A medical support bandage which comprises the construction material according to claim 1.

7. Moulded and shaped articles prepared by moulding or shaping construction material according to claim 1.

8. A filler or sealing material for joints and hollow spaces which comprises the construction material according to claim 1.

9. Process for preparing construction materials which comprises mixing a water-hardening reactive resin with 0.1 to 10% by weight polyether polysiloxane polyurethane additive of the formula

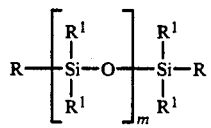

in which
$R^1$ is lower alkyl,
m is the average number of siloxane groups in the range from 5 to 25,
R is

in which
X is lower alkylene,
Y is an aliphatic, cycloatliphatic, aromatic or araliphatic moiety, which is unsubstituted or substituted by further

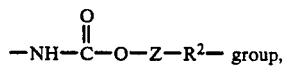 group,

Z is a polyether moiety based on ethylene oxide units, propylene oxide units, or both with the average number of ethylene oxide and propylene oxide units being in the range from 5 to 150 and $R^2$ is lower alkyl; adding catalysts and further additives and auxiliaries, and the mixture is then distributed homogeneously over the surface of a flexible substrate carrier material.

10. Water-hardening polymer preparations for construction materials comprising a water-hardening resin and 0.1 to 10% by weight polyether polysiloxane polyurethane additive of the formula

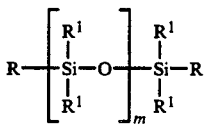

in which
$R^1$ is lower alkyl,
m is the average number of siloxane groups in the range form 5 to 25,
R is

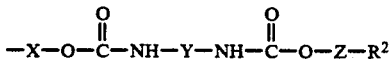

in which
X is lower alkylene,
Y is an aliphatic, cycloaliphatic, aromatic or araliphatic radical, moiety which is unsubstituted or substituted by further

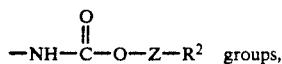 groups,

Z is a polyether moiety based on ethylene oxide units, propylene oxide units, or both with the average number of ethylene oxide and propylene oxide groups being in the range from 5 to 150 and $R^2$ is lower alkyl.

11. Water-hardening polymer preparations according to claim 10 containing polyether polysiloxane polyurethanes, in which $R^1$ is methyl or ethyl, m is the average number of siloxane groups in the range from 5 to 25, R is

in which

X is alkylene having 1 to 4 carbon atoms,

Y is an aliphatic hydrocarbon moiety having 2 to 18 carbon atoms, a cycloaliphatic hydrocarbon moiety having 4 to 15 carbon atoms, and wherein Y is unsubstituted by further

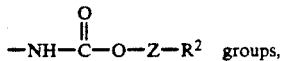 groups,

Z is a polyether moiety based on ethylene oxide units and propylene oxide units with the average number of ethylene oxide units and propylene oxide units being in the range from 5 to 150 and with the weight ratio of ethylene oxide units to propylene oxide units being 10:90 to 80:20, and $R^2$ is alkyl having 1 to 4 carbon atoms.

12. Water-hardening polymer preparations according to claim 11 wherein Y is an aliphatic hydrocarbon moiety having 6 to 10 carbon atoms, a cycloaliphatic hydrocarbon moiety having 5 to 10 carbon atoms, an aromatic hydrocarbon moiety having 6 to 13 carbon atoms, and wherein Y is unsubstituted or substituted by further

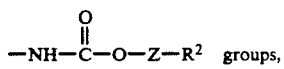 groups, and wherein Z is a polyether moiety based on ethylene oxide units and propylene oxide units with the average number of ethylene oxide units and propylene oxide units being in the range from 10 to 100 and the weight ratio of ethylene oxide units to propylene oxide units being 10:90 to 80:20.

13. Water-hardening polymer preparations according to claim 10 wherein the preparations contain 0.1 to 10% by weight of polyether polysiloxane polyurethanes, based on water-hardening polymer.

14. Water-hardening polymer preparations according to claim 11 wherein the resin is polyisocyanate, polyurethane or polyvinyl polymers.

15. Water-hardening polymer preparations according to claim 14 which contains polyisocyanates or prepolymers thereof with more than two isocyanate groups.

* * * * *